United States Patent [19]

Winkfein et al.

[11] Patent Number: 5,663,048
[45] Date of Patent: Sep. 2, 1997

[54] Y-CHROMOSOME SPECIFIC POLYNUCLEOTIDE PROBES FOR PRENATAL SEXING

[75] Inventors: Robert J. Winkfein; Gordon H. Dixon, both of Calgary, Canada

[73] Assignee: University of Calgary, Calgary, Canada

[21] Appl. No.: 330,537

[22] Filed: Oct. 27, 1994

Related U.S. Application Data

[63] Continuation of Ser. No. 30,485, filed as PCT/CA91/00353, abandoned.

[30] Foreign Application Priority Data

Oct. 4, 1990 [CA] Canada ................................. 2026926

[51] Int. Cl.$^6$ ................................. C12Q 1/68; C12P 19/34; C07H 21/04
[52] U.S. Cl. ................................. 435/6; 435/91.2; 536/24.3
[58] Field of Search ................................. 435/6, 91.2; 935/77, 935/78; 536/24.3, 24.31

[56] References Cited

U.S. PATENT DOCUMENTS

| | | | |
|---|---|---|---|
| 4,769,319 | 9/1988 | Ellis et al. | 435/6 |
| 4,960,690 | 10/1990 | Ellis et al. | 436/6 |
| 5,215,884 | 6/1993 | McGraw, III | 435/6 |

FOREIGN PATENT DOCUMENTS

| | | |
|---|---|---|
| 59561/86 | 12/1986 | Australia. |
| 1296270 | 2/1992 | Canada. |
| 1312565 | 1/1993 | Canada. |
| 8801300 | 2/1988 | WIPO. |
| 8907154 | 8/1989 | WIPO. |

OTHER PUBLICATIONS

Page et al., (1987) "The sex–determining region of the human Y chromosome encodes a finger protein" *Cell* 51: 1091–1104.

Mardon & Page (1989) "The sex–determining region of the mouse Y chromosome encodes a protein with a highly acidic domain and 13 zinc fingers" *Cell* 56: 765–770.

Koopman et al. (1989) "Zfy gene expression patterns are not compatible with a primary role in mouse sex determination" *Nature* 342:940–942.

Palmer et al. (1989) "Genetic Evidence that ZFY is not the testis–determining factor" *Nature* 342:937–939.

Burgoyne (1989) "Thumbs down for zinc finger?" *Nature* 342:860–862.

Leonard et al. (1987) "Sexing bovine embryos using Y Chromosome specific DNA probe" *Theriogenology* 27:248 (abstract).

Bondioli et al. (1989) "The use of male–specific chromosomal DNA fragments to determine the sex of bovine preimplantation embryos" *Theriogenology* 31:95–104.

Vaiman et al., (1988) "Sexing of bovine embryos using male–specific nucleic acid probes" *Third World Congress Sheep and Beef Cattle Breeding*. 93–105.

Matthews et al, Analyti. Biochem 169:1–25 (1988).

Maniatis et al, "Molecular Cloning" (1982) p. 388.

Nakahori et al., Am J. Med. Genetic 39: 472–973 (1991) "Sex Identification by PCR . . . ".

*Primary Examiner*—W. Gary Jones
*Assistant Examiner*—Eggerton Campbell
*Attorney, Agent, or Firm*—Burns, Doane, Swecker, & Mathis, L.L.P.

[57] ABSTRACT

Y-chromosome specific hybridization probes for prenatal sexing are provided capable of hybridizing only to Y-chromosome specific DNA sequences of bovine and other ruminants and are suitable for sexing embryos at or before the time of embryo transfer with essentially 100% accuracy.

30 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1872 base pairs
( B ) TYPE: nucleic acid
( C ) STRANDEDNESS: double
( D ) TOPOLOGY: linear ( x i ) SEQUENCE DESCRIPTION: SEQ ID NO:1:

| | | | | | |
|---|---|---|---|---|---|
| CTGCAGAGCT | TCAGGCAGGG | TTGGAAATGC | TCGCCCTGGA | CAGCTGAATG | AGTTCTGCCT | 60 |
| GCATTCTATA | TTCTCCCATT | ACCTTGGACA | GCTTCACAGT | ACCAGTCACA | CTGGCCTGAT | 120 |
| CCATTGCCTG | TGCATTCTCT | CAGGGGACCA | GAAAACAAGG | ACGTCTGGGC | TCAGCTGACT | 180 |
| TGGAGAACTG | CTTTCTCAGT | GTGCCCCTTC | TAAGTCATTC | CTGGTCAAAA | CTGTGTCCCT | 240 |
| ATTGCTAGCC | TACCACATCA | GCATTCTGAG | TGAGGTCCCC | TGTTCTTTCT | ACCTGTGTAG | 300 |
| TTTTCTGTGT | GCACCTGTCT | ACCTGTGCCT | CCAAGCACTA | TCTCCCTTTA | GCAGGAAAAG | 360 |
| ACCTGTGCCT | CCAAGCACTA | TCTCCCTTTA | GCAGGAAAAG | CCAAAGAGA | TGCCTGAGCC | 420 |
| TCCAAGGGCC | CCCAGAGTCT | GTGAGAGACC | TGGGTGTGAT | CCAATGTTGT | GAAGAAGGTG | 480 |
| CCCATAGATA | GAGGGTCTCT | TCTGAAACAA | GGCATGAAGC | CCGAGACCAT | AATGGTAAGG | 540 |
| TGGCATTCCT | ACAGGTGGTC | CCTTCTGTTT | ATTCCTACCC | AGACCCATGG | AGTCCCCAAA | 600 |
| CAGATGATGA | TCTGGGAATC | CTGCCCTTTC | TGGGCCCACA | GCTCATGCCT | CCCTTGGACA | 660 |
| GAAAGCAGCT | TTTCTATCTC | AAAAACACCA | AGAGGGCTTG | ATTCCACCCA | GGCCTCATTG | 720 |
| ATTTGCTAAA | TCAAATACTC | TCTTTCATTG | GGTTCATTAA | GCCCAGGTAG | GACTCCCTGG | 780 |
| AGTCAGGCAT | CCCTGCTTAC | CTACACAGCC | CACGTGCCAA | GTTAGCCAGT | CCTTGGTTGG | 840 |
| CCACAGGGGC | ATCCAAGACT | GTCACCTGGA | ATGCAGCTTC | CTTCTGAGTG | TCAGCTGGTG | 900 |
| CAGATCCCCT | ACGACAAAAT | CAGAGATTAT | GCTCCAGAGA | AACTGCCAAA | ATCCTCCCCC | 960 |
| AGGTGCAAAC | ACACACCTTT | GCCCTCAGGT | CCCCAAAGCC | AGGGGAAAGA | CCCAGAGAAA | 1020 |
| AGAAGGAATT | TATATCAGGA | CTTTCAGCAC | AAGCCATGGG | GTATCTTTGG | CAGGAGCGTT | 1080 |
| ATTGCCTTTC | CCCTGGACCC | TGAAAACCAG | CAGGCCCTAA | ACTGCACCCA | GGGGCTTCCC | 1140 |
| TGTCTCCCAC | TCTCATGAGG | TCCTTCAGAC | ACGCAATAAG | CCCATCATCC | TTGCTTCCTC | 1200 |
| CCTGTTCCCT | CCCTTATAGG | CACACCTCGG | CAGAAGAGCA | CACACGTAAA | ACACCTGCAC | 1260 |
| TTTCTACGCC | TTTCTGCACT | GCCAGGGAGA | CTGGAAGTGC | CTGGAGGCAT | GCCACACTCA | 1320 |
| CATCTTGTCT | CTCCTAGGAT | GCCTGTGGTT | TTGCACGACA | GCCTACCTTA | GCATGTCTCG | 1380 |
| CATTTGTGT | CACATCGTTC | CAGTGTGTGA | AACCCTCATG | GAGAGAGGGT | GCTGGCTGAT | 1440 |
| GGGCTGATCC | TGGGAAGCAC | TGGCCCAGGA | CCTTCCAGG | TCTCCTTCTC | ACATGTGTAG | 1500 |
| AGCAAGTCTC | CAGTACACAA | GTCAATCTGT | GCCTCTTTCT | CTTCGGGTCT | CTGTCCTTCT | 1560 |
| CAGCAAGACC | TTAGCCTCCT | CACCCATCCC | AGGTCCTCTG | TATCCACATC | CACCATTTCC | 1620 |
| GCCTGCCAGC | CCATGTCCCC | ACAGGCTGTG | GGCTCCACAG | GCGGTGGTTT | TAAAGCCTCA | 1680 |
| CTCCACCTGA | TTTGCCCTGG | GTGAATCCAC | AGACCATGCA | CTCACTCTTC | CTGGTCCAAA | 1740 |
| CACATACAAG | AACACGGTAG | AAATGGTGAG | TGTGTTTTG | TATTTCATCT | CATGGCAGAT | 1800 |
| TTCTGAAGCC | AAGGTCCTGA | GTTATCAGTG | GCCATCCTTT | CCTCATTCCC | ATCCTGGACA | 1860 |
| GGGTCACTGC | AG | | | | | 1872 |

( 2 ) INFORMATION FOR SEQ ID NO:2:

( i ) SEQUENCE CHARACTERISTICS:
( A ) LENGTH: 1872 base pairs
( B ) TYPE: nucleic acid
( C ) STRANDEDNESS: double
( D ) TOPOLOGY: linear ( x i ) SEQUENCE DESCRIPTION: SEQ ID NO:2:

| | | | | | |
|---|---|---|---|---|---|
| CUGCAGAGCU | UCAGGCAGGG | UUGGAAAUGC | UCGCCCUGGA | CAGCUGAAUG | AGUUCUGCCU | 60 |

```
GCAUUCUAUA UUCUCCCAUU ACCUUGGACA GCUUCACAGU ACCAGUCACA CUGGCCUGAU    120
CCAUUGCCUG UGCAUUCUCU CAGGGGACCA GAAAACAAGG ACGUCUGGGC UCAGCUGACU    180
UGGAGAACUG CUUUCUCAGU GUGCCCCUUC UAAGUCAUUC CUGGUCAAAA CUGUGUCCCU    240
AUUGCUAGCC UACCACAUCA GCAUUCUGAG UGAGGUCCCC UGUUCUUUCU ACCUGUGUAG    300
UUUUCUGUGU GCACCUGUCU ACCUGUGCCU CCAAGCACUA UCUCCCUUUA GCAGGAAAAG    360
ACCUGUGCCU CCAAGCACUA UCUCCCUUUA GCAGGAAAAG GCCAAGAGA UGCCUGAGCC     420
UCCAAGGGCC CCCAGAGUCU GUGAGAGACC UGGGUGUGAU CCAAUGUUGU GAAGAAGGUG    480
CCCAUAGAUA GAGGGUCUCU UCUGAAACAA GGCAUGAAGC CCGAGACCAU AAUGGUAAGG    540
UGGCAUUCCU ACAGGUGGUC CCUUCUGUUU AUUCCUACCC AGACCCAUGG AGUCCCAAA    600
CAGAUGAUGA UCUGGGAAUC CUGCCCUUUC UGGGCCCACA GCUCAUGCCU CCCUUGGACA    660
GAAAGCAGCU UUUCUAUCUC AAAAACACCA AGAGGGCUUG AUUCCACCCA GGCCUCAUUG    720
AUUUGCUAAA UCAAUACUC UCUUUCAUUG GGUUCAUUAA GCCCAGGUAG GACUCCCUGG     780
AGUCAGGCAU CCCUGCUUAC CUACACAGCC CACGUGCCAA GUUAGCCAGU CCUUGGUUGG    840
CCACAGGGGC AUCCAAGACU GUCACCUGGA AUGCAGCUUC CUUCUGAGUG UCAGCUGGUG    900
CAGAUCCCCU ACGACAAAAU CAGAGAUUAU GCUCCAGAGA AACUGCCAAA AUCCUCCCCC    960
AGGUGCAAAC ACACACCUUU GCCCUCAGGU CCCCAAAGCC AGGGGAAAGA CCCAGAGAAA   1020
AGAAGGAAUU UAUAUCAGGA CUUUCAGCAC AAGCCAUGGG GUAUCUUUGG CAGGAGCGUU   1080
AUUGCCUUUC CCCUGGACCC UGAAAACCAG CAGGCCCUAA ACUGCACCCA GGGGCUUCCC   1140
UGUCUCCCAC UCUCAUGAGG UCCUUCAGAC ACGCAAUAAG CCCAUCAUCC UUGCUUCCUC   1200
CCUGUUCCCU CCCUUAUAGG CACACCUCGG CAGAAGAGCA CACGUAAA ACACCUGCAC     1260
UUUCUACGCC UUUCUGCACU GCCAGGGAGA CUGGAAGUGC CUGGAGGCAU GCCACACUCA   1320
CAUCUUGUCU CUCCUAGGAU GCCUGUGGUU UUGCACGACA GCCUACCUUA GCAUGUCUCG   1380
CAUUUUGUGU CACAUCGUUC CAGUGUGUGA AACCCUCAUG GAGAGAGGGU GCUGGCUGAU   1440
GGGCUGAUCC UGGGAAGCAC UGGCCCAGGA CCUUCCCAGG UCUCCUUCUC ACAUGUGUAG   1500
AGCAAGUCUC CAGUACACAA GUCAAUCUGU GCCUCUUUCU CUUCGGGUCU CUGUCCUUCU   1560
CAGCAAGACC UUAGCCUCCU CACCCAUCCC AGGUCCUCUG UAUCCACAUC CACCAUUUCC   1620
GCCUGCCAGC CCAUGUCCCC ACAGGCUGUG GGCUCCACAG GCGGUGGUUU UAAAGCCUCA   1680
CUCCACCUGA UUUGCCCUGG GUGAAUCCAC AGACCAUGCA CUCACUCUUC CUGGUCCAAA   1740
CACAUACAAG AACACGGUAG AAAUGGUGAG UGUGUUUUUG UAUUUCAUCU CAUGGCAGAU   1800
UUCUGAAGCC AAGGUCCUGA GUUAUCAGUG GCCAUCCUUU CCUCAUUCCC AUCCUGGACA   1860
GGGUCACUGC AG                                                       1872
```

( 2 ) INFORMATION FOR SEQ ID NO:3:

( i ) SEQUENCE CHARACTERISTICS:
        ( A ) LENGTH: 3713 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GAGCTCGCTC TGTGTCTCTT TATCTCTGCT TCTGGCATAG CACTGTTTTG GGCTATCCTT     60
CTGTGTGTGT ACCAGGGCTG GTGTCTATGT AGTTCCATCT CTTTAAGTGA TGCTGTTACC    120
CTTTGCCACT GTCTGGACAC CAGCACTCAT ACGAGAAGCT TATCCTTGGC ATGAAGGCAA    180
GCCCTTCTCC TCCTGAGTGA GTTTCACTAA CGGGAGATCA GACTCTTTTT TAATTTAAAT    240
```

| | | | | | |
|---|---|---|---|---|---|
| TTATTTATTT | TAAGTAGAGG | CTAATTTACA | ATATTATATT | GGTTTTGCCA | TACATCAACA | 300
| TGAGTCCACC | ACGGGTGTAC | AAAATCAGAC | ATTTTTAGTC | CACACTTTCA | GACAGTACTT | 360
| TCTCAAACTT | GAAAGCCAAC | AGTGGGCGGT | CACTGCTGAA | CCTCAGAAGG | GGCCGGTTTA | 420
| TCCTCCCTCC | CTCACTGGAC | AGATGTGAAC | ACTGCACAGG | TCTGCAGCGT | CTTGGCCACA | 480
| CTTTGCACAG | AGGGAGAAAT | TGGGGCATGC | TCTGCTGGCA | TGAGGAAACT | CCCTGAACCT | 540
| TGTTCAAATG | CCTACCAGTG | AGATGCTAAG | GACAACTCCC | TGTTAAGTTC | CAGGACTTCC | 600
| TGGTGCCCGA | GACATGCACG | TCTGCCCATT | TACCCTACCA | AGGTCCTTTC | AAAATGGTTC | 660
| TGTTCTCCAT | GTAAGAACAC | GTACCAGCCT | GCCCAATAGG | CCAATCCTGT | GGGGCCAGGA | 720
| GCAGCAAGAG | GATCAAGCTA | ATCCATCCAT | CCTATAGTCC | TTACTCCCGA | TATATGCCTT | 780
| CTTCAAAGAG | TACAAAGAGT | ATTTTTCAAA | CTGGAAGACT | ATGCAGGTAG | CAGGTGCTTA | 840
| TGCTGCAGTG | CTGGTCCGTT | TCTGAAACCT | CAAAAAAGG | CAAGGGGTGC | TCATGCTCAT | 900
| GGCAAGGACA | GGGAAAGAAA | GCCCAGTGTT | CTAGAAGGAT | AGAACNCCCT | GGTAGCTGCA | 960
| TGTCCAAGGG | GCTGTGGGGC | CACCCACTAT | GACCTCTGTG | TATTGGAATT | GCAGCCTGTT | 1020
| CTGTGTCTCG | GATCCTCTGC | ACTCTCATTG | GTCACCCCCA | GGCACTTTCT | TCCTGCCTCT | 1080
| CCTTTCTGCC | AGGCATCCTG | GGTGCACCAC | TGTGATTCCA | CTTAGAAGTT | GCTCACTCAG | 1140
| TGAGATAACA | GGGATTGGCA | ACCCGGCTCC | AGTGCTTCTG | ATGGCCAGAG | CATGTACCTT | 1200
| TCCTATGGCT | TTTATGTTTT | CCCTATTCAA | CTTCATCAC | CTGGTTAGGT | CAGTTCTAC | 1260
| ACCTCATACT | CACAAGCATA | CTATCAGGCG | CTTTTCATGC | ATATATGCAC | ACACATGCGT | 1320
| GTGTACACAT | TAACATCCTG | AGAGGAAACT | TGCACATATA | CAGACATACA | AACTTCTTC | 1380
| TCCAGGAACA | TCAATTTTGG | TAAGCACCTG | ACTTCTTTG | TCCTGATTAT | TTTCTTTCAC | 1440
| TTTCTCATCG | ATCCTGTCAG | GTTACACTTC | TAACCCTTTG | ACTTAGCCTC | AAAGGTCACA | 1500
| AAATTTGGC | ATTTGCTCCT | GACAAGGACC | GATCTGCAGA | GCTTCAGGCA | GGGTTGGAAA | 1560
| TGCTCGCCCT | GGACAGCTGA | ATGAGTTCTG | CCTGCATTCT | ATATTCTCCC | ATTACCTTGG | 1620
| ACAGCTTCAC | AGTACCAGTC | ACACTGGCCT | GATCCATTGC | CTGTGCATTC | TCTCAGGGGA | 1680
| CCAGAAAACA | AGGACGTCTG | GGCTCAGCTG | ACTTGGAGAA | CTGCTTTCTC | AGTGTGCCCC | 1740
| TTCTAAGTCA | TTCCTGGTCA | AAACTGTGTC | CCTATTGCTA | GCCTACCACA | TCAGCATTCT | 1800
| GAGTGAGGTC | CCCTGTTCTT | TCTACCTGTG | TAGTTTTCTG | TGTGCACCTG | TCTACCTGTG | 1860
| CCTCCAAGCA | CTATCTCCCT | TTAGCAGGAA | AAGACCTGTG | CCTCCAAGCA | CTATCTCCCT | 1920
| TTAGCAGGAA | AAGGCCAAAG | AGATGCCTGA | GCCTCCAAGG | GCCCCAGAG | TCTGTGAGAG | 1980
| ACCTGGGTGT | GATCCAATGT | TGTGAAGAAG | GTGCCCATAG | ATAGAGGGTC | TCTTCTGAAA | 2040
| CAAGGCATGA | AGCCCGAGAC | CATAATGGTA | AGGTGGCATT | CCTACAGGTG | GTCCCTTCTG | 2100
| TTTATTCCTA | CCCAGACCCA | TGGAGTCCCC | AAACAGATGA | TGATCTGGGA | ATCCTGCCCT | 2160
| TTCTGGGCCC | ACAGCTCATG | CCTCCCTTGG | ACAGAAAGCA | GCTTTTCTAT | CTCAAAAACA | 2220
| CCAAGAGGGC | TTGATTCCAC | CCAGGCCTCA | TTGATTTGCT | AAATCAAATA | CTCTCTTTCA | 2280
| TTGGGTTCAT | TAAGCCCAGG | TAGGACTCCC | TGGAGTCAGG | CATCCCTGCT | TACCTACACA | 2340
| GCCCACGTGC | CAAGTTAGCC | AGTCCTTGGT | TGGCCACAGG | GGCATCCAAG | ACTGTCACCT | 2400
| GGAATGCAGC | TTCCTTCTGA | GTGTCAGCTG | GTGCAGATCC | CCTACGACAA | AATCAGAGAT | 2460
| TATGCTCCAG | AGAAACTGCC | AAAATCCTCC | CCCAGGTGCA | AACACACACC | TTTGCCCTCA | 2520
| GGTCCCCAAA | GCCAGGGGAA | AGACCCAGAG | AAAAGAAGGA | ATTTATATCA | GGACTTTCAG | 2580
| CACAAGCCAT | GGGGTATCTT | TGGCAGGAGC | GTTATTGCCT | TTCCCCTGGA | CCCTGAAAAC | 2640

-continued

| | | | | | |
|---|---|---|---|---|---|
| CAGCAGGCCC | TAAACTGCAC | CCAGGGGCTT | CCCTGTCTCC | CACTCTCATG | AGGTCCTTCA 2700 |
| GACACGCAAT | AAGCCCATCA | TCCTTGCTTC | CTCCCTGTTC | CCTCCCTTAT | AGGCACACCT 2760 |
| CGGCAGAAGA | GCACACACGT | AAAACACCTG | CACTTTCTAC | GCCTTTCTGC | ACTGCCAGGG 2820 |
| AGACTGGAAG | TGCCTGGAGG | CATGCCACAC | TCACATCTTG | TCTCTCCTAG | GATGCCTGTG 2880 |
| GTTTTGCACG | ACAGCCTACC | TTAGCATGTC | TCGCATTTTG | TGTCACATCG | TTCCAGTGTG 2940 |
| TGAAACCCTC | ATGGAGAGAG | GGTGCTGGCT | GATGGGCTGA | TCCTGGGAAG | CACTGGCCCA 3000 |
| GGACCTTCCC | AGGTCTCCTT | CTCACATGTG | TAGAGCAAGT | CTCCAGTACA | CAAGTCAATC 3060 |
| TGTGCCTCTT | TCTCTTCGGG | TCTCTGTCCT | TCTCAGCAAG | ACCTTAGCCT | CCTCACCCAT 3120 |
| CCCAGGTCCT | CTGTATCCAC | ATCCACCATT | TCCGCCTGCC | AGCCCATGTC | CCCACAGGCT 3180 |
| GTGGGCTCCA | CAGGCGGTGG | TTTTAAAGCC | TCACTCCACC | TGATTGCCC | TGGGTGAATC 3240 |
| CACAGACCAT | GCACTCACTC | TTCCTGGTCC | AAACACATAC | AAGAACACGG | TAGAAATGGT 3300 |
| GAGTGTGTTT | TTGTATTTCA | TCTCATGGCA | GATTTCTGAA | GCCAAGGTCC | TGAGTTATCA 3360 |
| GTGGCCATCC | TTTCCTCATT | CCCATCCTGG | ACAGGGTCAC | TGCAGAGATA | GGGCGACCAA 3420 |
| CCACCCTCAA | ACTGGGGGTG | CCTTGTGTCT | CGTCTTCTGA | TTGCTTGGCA | TTTCCTCTCC 3480 |
| TGTAGCCTTT | TTCTCTGATA | TTTCCCTGGG | CCACACACAC | ACACACACAC | ACACACAC 3540 |
| ACACACGCAC | GCAAACACAG | GTGACACAAG | CACACACGGT | ATACACACAC | AGGCTCGATA 3600 |
| CAGGGACACA | AACACAAACA | GGGAACACAG | GTGTTTCAGG | AGCTGAAGAC | GCCCATGTGT 3660 |
| CCAGCAGTAT | CAGAGATGGC | ATCAGTAGGC | ACCACGTCCT | GCACTTGGAG | CTC 3713 |

( 2 ) INFORMATION FOR SEQ ID NO:4:

( i ) SEQUENCE CHARACTERISTICS:
        ( A ) LENGTH: 3713 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

| | | | | | |
|---|---|---|---|---|---|
| GAGCUCGCUC | UGUGUCUCUU | UAUCUCUGCU | UCUGGCAUAG | CACUGUUUUG | GGCUAUCCUU 60 |
| CUGUGUGUGU | ACCAGGGCUG | GUGUCUAUGU | AGUUCCAUCU | CUUUAAGUGA | UGCUGUUACC 120 |
| CUUUGCCACU | GUCUGGACAC | CAGCACUCAU | ACGAGAAGCU | UAUCCUUGGC | AUGAAGGCAA 180 |
| GCCCUUCUCC | UCCUGAGUGA | GUUUCACUAA | CGGGAGAUCA | GACUCUUUUU | UAAUUUAAAU 240 |
| UUAUUUAUUU | UAAGUAGAGG | CUAAUUUACA | AUAUUAUAUU | GGUUUUGCCA | UACAUCAACA 300 |
| UGAGUCCACC | ACGGGUGUAC | AAAAUCAGAC | AUUUUUAGUC | CACACUUUCA | GACAGUACUU 360 |
| UCUCAAACUU | GAAAGCCAAC | AGUGGGCGGU | CACUGCUGAA | CCUCAGAAGG | GGCCGGUUUA 420 |
| UCCUCCCUCC | CUCACUGGAC | AGAUGUGAAC | ACUGCACAGG | UCUGCAGCGU | CUUGGCCACA 480 |
| CUUUGCACAG | AGGGAGAAAU | UGGGGCAUGC | UCUGCUGGCA | UGAGGAAACU | CCCUGAACCU 540 |
| UGUUCAAAUG | CCUACCAGUG | AGAUGCUAAG | GACAACUCCC | UGUUAAGUUC | CAGGACUUCC 600 |
| UGGUGCCCGA | GACAUGCACG | UCUGCCCAUU | UACCUACCA | AGGUCCUUUC | AAAAUGGUUC 660 |
| UGUUCUCCAU | GUAAGAACAC | GUACCAGCCU | GCCCAAUAGG | CCAAUCCUGU | GGGGCCAGGA 720 |
| GCAGCAAGAG | GAUCAAGCUA | AUCCAUCCAU | CCUAUAGUCC | UUACUCCCGA | UAUAUGCCUU 780 |
| CUUCAAAGAG | UACAAAGAGU | AUUUUUCAAA | CUGGAAGACU | AUGCAGGUAG | CAGGUGCUUA 840 |
| UGCUGCAGUG | CUGGUCCGUU | UCUGAAACCU | CAAAAAAAGG | CAAGGGGUGC | UCAUGCUCAU 900 |
| GGCAAGGACA | GGGAAAGAAA | GCCCAGUGUU | CUAGAAGGAU | AGAACNCCCU | GGUAGCUGCA 960 |

| | | | | | |
|---|---|---|---|---|---|
| UGUCCAAGGG | GCUGUGGGGC | CACCCACUAU | GACCUCUGUG | UAUUGGAAUU | GCAGCCUGUU | 1020
| CUGUGUCUCG | GAUCCUCUGC | ACUCUCAUUG | GUCACCCCA | GGCACUUUCU | UCCUGCCUCU | 1080
| CCUUUCUGCC | AGGCAUCCUG | GGUGCACCAC | UGUGAUUCCA | CUUAGAAGUU | GCUCACUCAG | 1140
| UGAGAUAACA | GGGAUUGGCA | ACCCGGCUCC | AGUGCUUCUG | AUGGCCAGAG | CAUGUACCUU | 1200
| UCCUAUGGCU | UUUAUGUUUU | CCCUAUUCAA | CUUCUAUCAC | CUGGUUAGGU | CAGUUUCUAC | 1260
| ACCUCAUACU | CACAAGCAUA | CUAUCAGGCG | CUUUCAUGC | AUAUAUGCAC | ACACAUGCGU | 1320
| GUGUACACAU | UAACAUCCUG | AGAGGAAACU | UGCACAUAUA | CAGACAUACA | AACUUUCUUC | 1380
| UCCAGGAACA | UCAAUUUUGG | UAAGCACCUG | ACUUUCUUUG | UCCUGAUUAU | UUUCUUUCAC | 1440
| UUUCUCAUCG | AUCCUGUCAG | GUUACACUUC | UAACCCUUUG | ACUUAGCCUC | AAAGGUCACA | 1500
| AAAUUUUGGC | AUUUGCUCCU | GACAAGGACC | GAUCUGCAGA | GCUUCAGGCA | GGGUUGGAAA | 1560
| UGCUCGCCCU | GGACAGCUGA | AUGAGUUCUG | CCUGCAUUCU | AUAUUCUCCC | AUUACCUUGG | 1620
| ACAGCUUCAC | AGUACCAGUC | ACACUGGCCU | GAUCCAUUGC | CUGUGCAUUC | UCUCAGGGA | 1680
| CCAGAAAACA | AGGACGUCUG | GGCUCAGCUG | ACUUGGAGAA | CUGCUUUCUC | AGUGUGCCCC | 1740
| UUCUAAGUCA | UUCCUGGUCA | AAACUGUGUC | CCUAUUGCUA | GCCUACCACA | UCAGCAUUCU | 1800
| GAGUGAGGUC | CCCUGUUCUU | UCUACCUGUG | UAGUUUCUG | UGUGCACCUG | UCUACCUGUG | 1860
| CCUCCAAGCA | CUAUCUCCCU | UUAGCAGGAA | AAGACCUGUG | CCUCCAAGCA | CUAUCUCCCU | 1920
| UUAGCAGGAA | AAGGCCAAAG | AGAUGCCUGA | GCCUCCAAGG | GCCCCAGAG | UCUGUGAGAG | 1980
| ACCUGGGUGU | GAUCCAAUGU | UGUGAAGAAG | GUGCCCAUAG | AUAGAGGGUC | UCUUCUGAAA | 2040
| CAAGGCAUGA | AGCCCGAGAC | CAUAAUGGUA | AGGUGGCAUU | CCUACAGGUG | GUCCCUUCUG | 2100
| UUUAUUCCUA | CCCAGACCCA | UGGAGUCCCC | AAACAGAUGA | UGAUCUGGGA | AUCCUGCCCU | 2160
| UUCUGGGCCC | ACAGCUCAUG | CCUCCCUUGG | ACAGAAAGCA | GCUUUCUAU | CUCAAAAACA | 2220
| CCAAGAGGGC | UUGAUUCCAC | CCAGGCCUCA | UUGAUUUGCU | AAAUCAAAUA | CUCUCUUUCA | 2280
| UUGGGUUCAU | UAAGCCCAGG | UAGGACUCCC | UGGAGUCAGG | CAUCCUGCU | UACCUACACA | 2340
| GCCCACGUGC | CAAGUUAGCC | AGUCCUUGGU | UGGCCACAGG | GGCAUCCAAG | ACUGUCACCU | 2400
| GGAAUGCAGC | UUCCUUCUGA | GUGUCAGCUG | GUGCAGAUCC | CUACGACAA | AAUCAGAGAU | 2460
| UAUGCUCCAG | AGAAACUGCC | AAAAUCCUCC | CCCAGGUGCA | ACACACACC | UUUGCCCUCA | 2520
| GGUCCCCAAA | GCCAGGGGAA | AGACCCAGAG | AAAAGAAGGA | AUUUAUAUCA | GGACUUUCAG | 2580
| CACAAGCCAU | GGGGUAUCUU | UGGCAGGAGC | GUUAUUGCCU | UCCCCUGGA | CCCUGAAAAC | 2640
| CAGCAGGCCC | UAAACUGCAC | CCAGGGGCUU | CCCUGUCUCC | CACUCUCAUG | AGGUCCUUCA | 2700
| GACACGCAAU | AAGCCCAUCA | UCCUUGCUUC | CUCCCUGUUC | CCUCCCUUAU | AGGCACACCU | 2760
| CGGCAGAAGA | GCACACACGU | AAAACACCUG | CACUUUCUAC | GCCUUUCUGC | ACUGCCAGGG | 2820
| AGACUGGAAG | UGCCUGGAGG | CAUGCCACAC | UCACAUCUUG | UCUCUCCUAG | GAUGCCUGUG | 2880
| GUUUUGCACG | ACAGCCUACC | UUAGCAUGUC | UCGCAUUUUG | UGUCACAUCG | UUCCAGUGUG | 2940
| UGAAACCCUC | AUGGAGAGAG | GGUGCUGGCU | GAUGGGCUGA | UCCUGGGAAG | CACUGGCCCA | 3000
| GGACCUUCCC | AGGUCUCCUU | CUCACAUGUG | UAGAGCAAGU | CUCCAGUACA | CAAGUCAAUC | 3060
| UGUGCCUCUU | UCUCUUCGGG | UCUCUGUCCU | UCUCAGCAAG | ACCUUAGCCU | CCUCACCCAU | 3120
| CCCAGGUCCU | CUGUAUCCAC | AUCCACCAUU | UCCGCCUGCC | AGCCCAUGUC | CCCACAGGCU | 3180
| GUGGGCUCCA | CAGGCGGUGG | UUUUAAAGCC | UCACUCCACC | UGAUUUGCCC | UGGGUGAAUC | 3240
| CACAGACCAU | GCACUCACUC | UUCCUGGUCC | AAACACAUAC | AAGAACACGG | UAGAAAUGGU | 3300
| GAGUGUGUUU | UUGUAUUUCA | UCUCAUGGCA | GAUUUCUGAA | GCCAAGGUCC | UGAGUUAUCA | 3360

-continued

| | | | | | | |
|---|---|---|---|---|---|---|
| GUGGCCAUCC | UUUCCUCAUU | CCCAUCCUGG | ACAGGGUCAC | UGCAGAGAUA | GGGCGACCAA | 3420 |
| CCACCCUCAA | ACUGGGGGUG | CCUUGUGUCU | CGUCUUCUGA | UUGCUUGGCA | UUUCCUCUCC | 3480 |
| UGUAGCCUUU | UUCUCUGAUA | UUUCCCUGGG | CCACACACAC | ACACACAC | ACACACACAC | 3540 |
| ACACACGCAC | GCAAACACAG | GUGACACAAG | CACACACGGU | AUACACACAC | AGGCUCGAUA | 3600 |
| CAGGGACACA | AACACAAACA | GGGAACACAG | GUGUUUCAGG | AGCUGAAGAC | GCCCAUGUGU | 3660 |
| CCAGCAGUAU | CAGAGAUGGC | AUCAGUAGGC | ACCACGUCCU | GCACUUGGAG | CUC | 3713 |

Y-CHROMOSOME SPECIFIC POLYNUCLEOTIDE PROBES FOR PRENATAL SEXING

This application is a continuation of application Ser. No. 08/030,485, filed May 13, 1995, now abandoned, which is the National Stage under 35 U.S.C. §371 of International Patent Application Ser. No. PCT/CA91/00353, filed on Oct. 3, 1991, which claims priority to Canada Patent Application No. 2,026,926, filed on Oct. 4, 1990.

FIELD OF THE INVENTION

The present invention relates to determination of genetic sex of mammals, more particularly to ruminant sex determination using Y-specific polynucleotide probes.

BACKGROUND OF THE INVENTION

The ability to determine the sex of an embryo soon after fertilization would provide numerous advantages in the livestock and dairy industries as well as in veterinary medicine. In the dairy and beef cattle industry advances in embryo transfer has resulted in a great demand for a method of quickly determining the sex of embryos and cells taken from embryos at early stages of development. The commercial efficiency of livestock and dairy operations would be greatly improved by allowing gestation to be established with embryos of the desired sex. Given the advantage to the dairy industry of a preponderance of female progeny, it would be advantageous if the sex of embryos could be routinely determined prior to embryo transplant into a maternal host. The advantages of sexed embryos are numerous including the selection of replacement of stock based on desired characteristics, such as size, weight, increased milk production, etc. In addition, certain diseases, such as X-chromosome-linked diseases in humans and similar diseases in other mammals, affect individuals of only one sex. Early determination of the sex of an embryo which, if carried to term, would likely be an individual with such a disease would be particularly advantageous and provide valuable information on which to base a decision to allow further development.

Efficient determination of the sex of a conceptus in vivo is also of significant economic importance, and would have important commercial applications. In the dairy and livestock industries, in pregnancies which arise via artificial insemination or natural mating, early determination of the sex of an embryo or fetus would allow for termination of the pregnancy if an embryo or fetus of the desired sex was not obtained.

In situations where, for health or economic reasons, a determination of the sex of an embryo or fetus is indicated, it is important to determine the sex as soon as possible after fertilization. There is a substantial increase in risk to the life and health of a female if abortion is induced late in gestation. With livestock, it is commercially inefficient, both because of reduced reproductive efficiency and dangers to the life and health of the female, to carry an embryo longer than necessary.

With advances in reproductive biology, it would be feasible to avoid all risks and costs associated with pregnancy and abortion if it were possible to determine the sex of an embryo, whether produced in vivo or in vitro prior to or at the time of transfer, and also to determine as early as possible with certainty the sex of an embryo or fetus in vivo.

The sex of a mammal is determined by the presence or absence of the entire Y-chromosome or some functional portion thereof. Genes present on the Y-chromosome govern formation and the development of the male phenotype. The sex of an individual mammal is therefore dependent upon whether or not its genome contains particular DNA sequences, especially those sequences comprising that part of the Y-chromosome which encode genes responsible for sex determination.

The sex or presumptive sex of a mammal can therefore be determined by analysis for Y-specific genes in the DNA of the individual mammal. Alternatively, sex can be determined by unrelated but genetically linked sequences which are associated specifically with the Y-chromosome, preferably on sequences linked closely to the male-determining genes to reduce possible errors in analysis due to genetic recombination.

Prior to the present invention a number of investigators have identified DNA sequences which hybridize preferentially or exclusively to male DNA. See Kunkel et al., Science 191, 1189–1190 (1976); Bishop et al., Nature 303, 831 (1983); Vergnaud et al., Brit. Med. J. 289, 73–76 (1984); Lau et al., The Lancet, Jan. 7, 1984, pp 14–16; Gosden et al., The Lancet, Dec. 25, 1982, pp 1416–1419; Bostick et al., Nature 272, 324 (1978). These DNA sequences have not been functionally characterized, and it is unknown whether these sequences are capable of hybridization to non-human species.

The isolation of sperm separated according to the sex chromosome they contain, and using these sperm to fertilize ova is one method currently used to control embryo-sex. Such sperm isolation methods are significantly limited due to the difficulty of obtaining preparations of sperm in which more than 99% of the sperm carry the sex chromosome of only one of the sexes. At present, known techniques for separating sperm according to sex are not practical for obtaining mixtures of sperm with more than about 75% harboring the same sex chromosome. Therefore determining sex by segregating sperm is limited by economic and commercial considerations.

Karyotyping fetal cells obtained after several weeks gestation by amniocentesis, chorion biopsy, and other procedures is another known method of determining sex. Such procedures are limited, however, in commercial application due to the expense, risk of infection, and time required to carry out this type of analysis.

Other prior art attempts to deal with this problem have been indirect and incomplete. U.S. Pat. No. 4,769,319 issued to Ellis et al. discloses male specific nucleic acid hybridization probes which have sequences complementary to sequences of segments in bovine male specific DNA. These nucleic acid sequences are stated to be useful as hybridization probes for sexing embryos and fetuses. Australian Patent Application No. 59561/86 discloses bovine DNA probes which hybridize preferentially to male DNA, and are also stated to be useful in sexing embryos and fetuses. These DNA sequences are indicated to be species specific. International Patent Application No. PCT/AU87/00254, discloses a 307 base pair nucleic acid sequence designated BRY.1 comprising Y-specific DNA which is capable of hybridizing with male bovine and ovine derived DNA but not with DNA isolated from female animals. PCT Application No. PCT/AU 89/0029 discloses nucleic acid isolates capable of hybridizing to Y-specific DNA sequences of ruminants.

Moreover, there is nothing in the prior art to indicate that any like DNA segments exist which could be used to provide the basis of a polynucleotide probe to sex by nucleic acid hybridization, with as few as 2 cells, with virtually 100% accuracy, in an extremely short time period, a mammalian embryo at a morula or blastocyst stage, at or before transfer of the embryo for further development.

SUMMARY OF THE INVENTION

The present invention arises from the discovery of segments of Y-chromosome specific DNA sequences, designated SEQ ID NO:1; BtY1 and SEQ ID NO:3; BtY2 and corresponding RNA sequences that make possible the rapid, virtually 100% accurate sexing of bovine embryos by nucleic acid hybridization with an amount of DNA equal to the amount obtained from 2 or fewer embryonic cells. The sequences are repeated to varying degrees, with a repeat number differing between unrelated species, and are stably inherited. Furthermore, with the nucleic acid probes of this invention embryos may be sexed in less than one day at an early stage, at or before the time embryo transfer is carried out. With the present invention, the benefits of early and essentially certain sexing of bovine embryos can be achieved.

The present invention accomplishes this by providing sensitive Y-chromosome probes, designated SEQ ID NO:1; BtY1 and SEQ ID NO:3; BtY2, making possible the rapid, reliable, and economical sexing of cells obtained from an embryo. Probes of the present invention, which are sufficiently sensitive to sex a ruminant/bovine with DNA from as few as 2 of its cells, can also be used to sex fetuses and embryos. While sexing of fetuses by nucleic acid hybridization or karyotyping is essentially 100% accurate, it occurs after several weeks of gestation and involves significant risks to the fetus and mother. Thus, these known procedures for sexing fetuses have significant disadvantages compared with early embryo sexing made possible by the present invention.

The polynucleotide probes of the present invention were described through their association with male bovine DNA. Certain of these sequences are more efficacious than the prior art for determining the genetic sex of ruminants due to their preferential binding to male, in comparison to female, DNA of species of the genus Bos (bovine). Their superiority also results because they exist in higher copy number, are present in multiple copies in males but not in females, and show stronger sequence similarity between individual elements than have been sequenced.

In addition, the present invention encompasses methods for applying such DNA sequences in determining the sex of ruminant/bovine and isolating, from male DNA of such species, nucleic acid sequences which hybridize to significantly greater extent with the nucleic acids of the male rather than the female of the species. Such sequences provide for nucleic acid hybridization probes for sexing embryos and cells.

DEFINITIONS AND ABBREVIATIONS

DNA—deoxyribonucleic acid
RNA—ribonucleic acid
  A-adenine
  T-thymine
  G-guanine
  C-cytosine
  U-uracil
  Polynucleotide—single or double-stranded DNA or RNA
EDTA Ethylenediamine tetra acetate
Tris Tris (hydroxymethyl) amino methane
rpm rotations per minute
mM millimolar, Molar
mm millimeter
O.D. Optical density measured at× nanometers
DEAE Diethyl amino ethane
TE 10 mM Tris HCl pH 8.0 1 mM EDTA
DTT Dithiothreitol
M9 minimal plates, see Maniatis et.al. (1982) Molecular Cloning, A Lab Manual for formula
LB Luria Bertani broth
ATP Adenosine triphosphate
amp ampicillin cased at 150 mg/ml
SSPE See Maniatis et.al.
Denhardts (100× formula in Maniatis et.al)
SDS Sodium dodecyl sulphate

DETAILED DESCRIPTION OF PREFERRED EMBODIMENTS OF INVENTION

The present invention includes nucleic acids which are useful as hybridization probes for prenatally sexing mammals; the probes may be labeled so as to be detectable in a hybridization methodology or utilized in unlabeled form; methods of isolating and identifying such nucleic acids and probes; and procedures for using the probes in prenatal sexing of mammals are also disclosed.

The nucleic acid sequences of this invention can be single-stranded or double stranded DNA or RNA, or hybrids between DNA and RNA. The sequences may be labeled or unlabeled. The sequence of the labeled nucleic acid is the sequence the nucleic acid would have if each labeled nucleotide in the sequence were replaced with the corresponding unlabeled nucleotide. For example, if a DNA is labeled with a non-radioactive marker such as biotin on the 5-position of deoxyuridylate residues, the sequence of the labeled DNA is the same as that of the DNA where all of the biotin labeled deoxyuridylate are replaced with thymidylates. The sequences of a DNA and a RNA are the same if every deoxyribonucleotide, except thymidylate in the DNA is replaced with the corresponding ribonucleotide in the RNA and every thymidylate in the DNA is substituted in the RNA by uridylate.

The preferred nucleic acid probes, according to the invention, hybridize to a significantly greater extent with total male DNA than total female DNA of a bovine species, when hybridizations are carried out under similar conditions. The probes of this invention will not hybridize detectably to total female bovine DNA in an hybridization under stringent conditions over a hybridization period during which detectable hybridizations with total male bovine DNA occur.

Preferably the nucleic acid probes, according to the invention, are hybridized under stringent conditions with chromosomal DNA derived from cells of an embryo of the species being tested. The probes correspond to all or part of a DNA sequence found on the Y-chromosome of at least one of bovine, ovine, and caprine animals.

The fundamental feature of the nucleic acids of the invention, both unlabeled and labeled, is that, when in single stranded form, they hybridize with a probability greater than 0.99 preferentially with total male DNA rather than total female DNA of a bovine species under substantially the same hybridization conditions.

In particular, there are provided and defined two nucleic acid isolates from male bovine that are capable of hybridizing only to sequences of nucleic acid from bovine which contain the Y-chromosomal DNA sequences. The nucleic acid isolates correspond to DNA sequences comprising part of the Y-chromosomal DNA of bovine mammals, and are referred to as SEQ ID NO:1; BtY1 and SEQ ID NO:3; BtY2, respectively.

It is well known in the nucleic acid hybridization probe art that nucleic acids with different sequences may, under the same conditions, hybridize detectably to the same "target" nucleic acid. Two nucleic acids hybridize detectably, under stringent conditions over a sufficiently long hybridization period because one comprises a segment of at least about 12 nucleotides in a sequence complementary or nearly complementary to the sequence of at least one segment of the target nucleic acid. The physical basis for hybridization is base-pairing between these complementary or nearly complementary segments. If the time during which hybridization is allowed to occur is held constant, at a value which, under stringent conditions, two nucleic acids with exactly complementary base-pairing segments hybridize detectably to each other, increasing departures from exact complementarity can be made into the base-pairing segments, but sufficient base pairing will still occur to an extent to make hybridization detectable, as the base-pairing segments of two nucleic acids becomes larger and as the conditions of the hybridization become less stringent. Moreover, segments outside of the probing segment of a probe nucleic acid may be altered significantly in sequence without substantially diminishing the extent of hybridization between the probe and its target so long as the alteration does not introduce a probing segment complementary or nearly complementary to a target segment in a different target present in samples to be probed. If segments outside the probing segment are changed substantially in length, the rate of hybridization may also be altered. The term "substantially the same sequence" is used within the meaning of the present specification to mean that two single stranded nucleic acid segments (a) both form a base-paired duplex with the same segment, and (b) the melting temperatures of said two duplexes in a solution of 0.5× SSPE differ by less than 10 degrees Celsius. Two double-stranded nucleic acid segments have "substantially the same sequence" if either strand of one of the segments has "substantially the same sequence" as one of the strands of the other segment. Any labeling method known in the art would be suitable in the practice of the present invention.

Application of a nucleic acid as a hybridization probe in accordance to the invention may be made by the labeling of the probe in order to facilitate detection. Preferably the nucleic acids of the invention are detectably labeled with a non-radioactive label such as biotin. Other non-radioactive labels such as bromodeoxyuridine may also be used.

Radioactive isotopes may also be used for labeling the nucleic acid probes of this invention. Preferably the probes are labeled with 32P. However, other radioactive labels may also be conveniently employed such as $^3H$, $^{14}C$, $^{13}$, or $^{125}I$. Labeling may be easily accomplished by nick-translating a sample of the DNA for example, in the presence of one or more deoxy-nucleoside-5-triphosphates which are labeled with the isotope.

An alternative to the use of non-radioactive or radioactive labels is the chemical labeling of the nucleic acid of this invention. For example, conventional nick-translation of the nucleic acid in the presence of deoxyuridylate biotinylated at the 5-position of the uracil moiety to replace thymidylate residues is suitable. The resulting labeled probe will include the biotinylated uridylate in place of thymidylate residuals. The resulting labeled probe will include biotinylated uridylate in place of thymidylate residues and is detectable via the biotin moieties by any of a number of commercially available detection systems utilizing the binding of streptavidin to the biotin. See, for example, Singer and Ward, Proc. Natl. Acad. Sci. U.S.A. 79, 7331–7335 (1982). Detection systems are commercially available from, e.g., Bethesda Research Laboratories, Inc., Gaithersburg, Md., U.S.A. and Enzo Biochemicals, Inc., New York, N.Y., U.S.A.

The present invention also includes any contiguous portion of 12 or more nucleotides or any and all of the sequences illustrated in SEQ ID NOS: 1–4. Such nucleic acids may be used as hybridization probes to detect any of the illustrated sequences or similar sequences in bovine and non-bovine species. Such nucleic acid sequences may also be constructed synthetically using commercially available DNA synthesizers, such as the Applied Biosystems 380A DNA Synthesizer, obtained from Applied Biosystems, Inc., Foster City, Calif., U.S.A. Such nucleic acid probes which comprise less than about 12 nucleotides have limited usefulness as hybridization probes. Therefore the preferred probes, according to the invention, are those nucleic acid isolates comprising any contiguous portion of 12 or more nucleotides of any and all of the sequences described herein. Various embodiments include the use of recombinant DNA molecules constructed from all or part of the shown sequences and include a vector capable of propagation in host prokaryotic or eukaryotic cells for the purpose of cloning, amplification and/or expression of the claimed sequences. Any number of a wide range of vector molecules may be used depending on the intended use of the nucleic acid. Examples of such vectors include molecules such as pT218u or pTZ19u, and BLUESCRIPT (Stratagene), however, vector molecules include both eukaryotic and prokaryotic vectors, plasmids, phagemids, shuttle vectors, bacteriophage, and the like.

RNA corresponding to all or part of the sequences as described may be produced using any method well known in the art including but not limited to in vitro transcription systems, utilizing for example, the RNA polymerases of bacteriophage. Numerous commercially available polymerases are suitable such as T3, T7 or SP6. See Melton, et al. Nuc. Acid. Res., 12, 7035–7056 (1984), and Taylor, et al. Biochem. Biophys. Acta 442, 324–330. Therefore, in various embodiments, the nucleic acid isolates of the invention include both DNA and RNA sequences which preferentially hybridize to Y-chromosome-specific DNA and RNA sequences and hence are useful in the determination of the genetic sex of a mammal.

SEQ ID NO:1; BtY1 is a 1.859 kb PstI fragment cloned from bovine DNA. The restriction fragment SEQ ID NO:1; BtY1 was sub-cloned and subsequently shown by hybridization to Southern blots of genomic DNA from individual male and female mammals to be generally conserved, male-specific, and repeated in bovines and other ruminants. SEQ ID NO:2 shows double-stranded RNA corresponding to the DNA sequence of SEQ ID NO:1; BtY1 where thymidine of the corresponding DNA in SEQ ID NO:1; BtY1 is replaced by uracil.

SEQ ID NO:3; BtY2 is a 3.71 kb SacI fragment cloned bovine DNA. The SEQ ID NO:1; BtY1 fragment was used to isolate SEQ ID NO:3; BtY2 and is contained within the SEQ ID NO:3 BtY2 fragment. The SacI restriction fragment of SEQ ID NO:3; BtY2 was sub-cloned and subsequently shown by hybridization to Southern blots of genomic DNA from individual male and female mammals to be generally conserved. SEQ ID NO:4 shows double-stranded RNA corresponding to the DNA sequence of SEQ ID NO:3; BtY2 where thymidine of the corresponding DNA in SEQ ID NO:3 BtY2 is replaced by uracil, and repeated in bovines.

The terms SEQ ID NO:1 BtY1 and SEQ ID NO:3; BtY2 refer to, where provided, the specific sequences set forth in SEQ ID NOS:1 and 3. These terms also include closed circularized and linearized SEQ ID NO:1; BtY1 and SEQ ID NO:3; BtY2 and variants where nucleotides have been substituted, added to, or deleted from, the relevant sequences shown, so long as the variants hybridize with all or part of any of the sequences SEQ ID NOS:1–4. Such variants may be naturally occurring allelic and/or cis variants which may arise within a population of individuals by virtue of insertions, deletions, or point mutations of DNA sequences, by recombination or by rearrangement. Alternatively, such variants may be artificially produced, for example, by deletion of fragments of DNA by exonuclease, by site-directed mutagenesis, or by the addition of DNA sequences by ligating portions of DNA together, or template-independent or template-dependent DNA polymerase.

Making and using the nucleic acids of the invention are described in detail in the following examples.

The nucleic acid isolates, according to the preferred embodiment, are used as hybridization probes to detect Y-chromosome specific DNA and RNA sequences and therefore the sex of, for example, embryo or fetal cells of bovine or other ruminants. In a related application, the nucleic acid probes of this invention may be used to detect variations in amounts and/or variations in sequence of corresponding sequences in individual mammals. Such applications are useful in, for example, paternity testing of male offspring. Various types of cells may be analyzed using the nucleic acid isolates and methods described herein, a useful example being their application to fractionated sperm where various fractions may be tested for sperm bearing a Y-chromosome using the nucleic acid isolates of the present invention.

In a preferred method of determining the sex of an embryo, fetus, or the sex chromosome content of sperm or other cells using the nucleic acid probes of the invention, a sample of cells is removed for assay. DNA and/or RNA may be extracted therefrom using known methods. See Maniatis, et al. (1982) Molecular Cloning, A Laboratory Manual, Cold Spring Harbor Laboratory. The isolated DNA and/or RNA may then be applied and fixed directly to a membrane such as nitrocellulose, or a derivative thereof. Alternatively, the DNA and/or RNA may be electrophoresed through a gel matrix and then transferred and fixed to a similar membrane.

The nucleic acids so bound to the membrane are then hybridized with any or all of the nucleic acid isolates of the invention which are labeled with a detectable marker as previously described. The labeled nucleic acid isolate which binds to nucleic acid on the membrane is detected by conventional techniques well known in the art, for example, by autoradiography. If the labeled isolate hybridizes to similar sequences in the target sample, sex can be conclusively designated as male. Using this method, amplified target DNA may be used. See Saiki, et al., Science 230, 1350–1354 (1986), and Saiki, et al., Nature 324, 163–166 (1986).

An alternative method using the nucleic acid probes of the invention utilizes nucleic acids which are not extracted from the sample of cells removed for assay. Such cells are heated in alkaline solution and the resultant solution is filtered onto a charge-modified nylon membrane such as a ZETA-PROBE membrane (trademark of Bio-Rad). DNA fixed to the membrane is hybridized with nucleic acid isolate(s) of the invention as described in the method described above.

Another method, according to an embodiment of the invention, is useful for the determination of the sex chromosome constitution of a tissue or cell sample comprising, isolating DNA from the tissue or cell sample, immobilizing the isolated DNA onto a support matrix, hybridizing the immobilized DNA with a nucleic acid isolate of this invention, washing the unbound nucleic acid isolate from the support matrix, and then detecting the binding of the nucleic acid isolate to the bound DNA by conventional methods. If determining the Y-chromosome presence or absence in interphase of metaphase chromosome, or in fixed cells, a preferred methodology comprises hybridizing chromosome spreads of such cells with the Y-chromosome specific nucleic acid isolates of the invention under conditions enabling the nucleic acid isolate to bind to complementary DNA sequences. Unbound nucleic acid is washed away, and detecting binding of the nucleic acid isolates using conventional techniques of in situ hybridization, such as those described in Saiki, et al., Science 230, 324, 163–166 (1986), may be applied.

Conventional methods useful for amplifying the levels of target DNA may also be utilized in combination with the nucleic acid probes of the invention. For example, DNA isolated from the tissue or cell sample is denatured to separate the respective coding and non-coding strands, annealing the denatured DNA with a synthetic polynucleotide corresponding to 12 or more nucleotides from any of the nucleic acid probe sequences of the invention, incubating the annealed DNA with DNA polymerase to to extend the polynucleotide through the sequences, and repeating this sequence as many times as desired to amplify levels of target DNA. Subsequent detection of the target DNA in the amplified sample may be made by any number of conventional methods well known in the art. For example, immobilizing the DNA onto a support matrix, hybridizing the immobilized DNA with a nucleic acid of the invention under conditions permitting the labeled nucleic acid probe to bind to complementary sequences, washing unbound probe from the support matrix, and then detecting binding of the nucleic acid probe to the bound DNA. Alternatively, if labeled nucleotide precursors are used in the incubation with the DNA polymerase, the sample may be fractionated by electrophoresis in a gel matrix with subsequent detection of the labeled target DNA sequences. Hybridizations are carried out under standard conditions well known in the art. See Maniatis et al., (1982), Molecular Cloning, A Laboratory Manual, Cold Spring Harbor Laboratory.

Amplification of target DNA using polymerase chain reaction (PCR) prior to hybridization with the nucleic acid probes of the invention is another method useful in determining the sex of an embryo, fetus, or the like. Polynucleotide primers from a target sequence are used to amplify the DNA sequence occurring between the primer sequence of the target DNA. The amplified target sequences may be detected following their fixation to a membrane and analyzed using conventional hybridization techniques as previously described. The amplified target sequences may also be visualized using electrophoresis where the sequence is immobilized and stained in the gel matrix using standard stains such as silver reagent or ethidium bromide and subsequent visualization under ultraviolet light.

The nucleic acid isolates of the invention may be further used to comprise or form part of a kit for detecting the presence or absence of Y-chromosome specific sequences in a wide variety of tissue or cell samples. The nucleic acid isolates may be labeled with a wide variety of labels including radioactive or non-radioactive markers. The kits may also comprise a well known number of suitable components including but not limited to buffers for diluting reagents, labeled compounds, solid support for assays, and the like.

EXPERIMENTAL EXAMPLES

Preparation of Genomic DNA

Blood samples (FML) were collected by accepted veterinary procedures in sterile containers (VACUTAINER-Becton-Dickinson) containing 0.07 ml of 15% potassium EDTA and transferred into sterile 50 ml culture tubes. Red blood cells were lysed by the addition of 35 ml of 17 mM Tris HCl, pH 7.65, 140 mM ammonium chloride solution (prewarmed to 37 deg. C.) and incubated at 37 deg. C. for 10 minutes. Samples were centrifuged at 2,000 rpm in the swinging bucket rotor of an IEC CENTRA-8R centrifuge at 4 deg. C. for 10 minutes. The pellet, consisting mainly of nucleated white cells, was resuspended in saline (0.85% NaCl in sterile $H_2O$) and spun as above. Saline supernatant was removed and the pellet was resuspended in 2 ml of 100 mM Tris HCl, pH 8.0, 40 mM sodium EDTA. An equal volume of lysis mixture (100 mM Tris HCl, pH 8.0, 40 mM EDTA and 0.2% SDS) was added and the sample was chilled overnight at 4 deg. C. Four ml of 10 mM Tris HCl, pH 8.0, to which Proteinase K (Boehringer Mannheim) was added to a concentration of 1 mg per ml was added to the lysed cell suspension and incubated at 65 deg. C. for 2 hours with intermittent mixing. Standard phenol chloroform isoamyl alcohol (PCI) extraction was performed as follows: Redistilled phenol (BRL) was saturated with Tris HCl, pH 8.0, until the pH of the phenol was raised above pH 7.5. Hydroxyquinoline was added to 0.1%. Phenol was added to an equal volume of chloroform; isoamyl alcohol (24:1). The mixture (PCI) was added, in equal volume, to the sample to be extracted. Genomic DNA: PCI mixtures were mixed by slow rotation (50 rpm on a commercial rotating device) for 20 minutes. All other DNA's were mixed with PCI by vigorous vortexing. Samples were spun at 10,000 rpm in a HB4 rotor of a SORVALL centrifuge for 10–20 minutes at room temperature. The upper, aqueous phase containing DNA was removed with a wide-bore pipette and reextracted sequentially as above until no interphase was detectable between the aqueous DNA phase and the organic PCI phase. DNA was precipitated by the addition of 1/10th volume of 3M sodium acetate (pH 7.0) and 2–2.5 volumes 95% ethanol. Genomic DNA was pelleted by centrifugation at 5,000 rpm in an HB4 rotor at 4 deg. (all other DNA's were pelleted at 10,000 rpm). Ethanol was removed and the DNA was redissolved in 1 ml sterile $H_2O$ and reprecipitated as above. These pellets were washed two times with 70% ethanol, dried in vacuo and dissolved in sterile $H_2O$. DNA concentration was determined by measuring the O.D. 260 in a spectrophotometer. Genomic DNA was stored at 4 deg. C. until use (all other DNA's were stored frozen −20 deg. C.).

Genomic DNA (50–100ug) was digested with a four-fold excess (i.e. 4U enzyme/ug DNA) of either PstI or SacI restriction endonucleases (New England Biolabs), in buffers supplied by the manufacturer, for 4 hours at 37 deg. C. Digested DNA was purified by standard PCI extraction and ethanol precipitation. DNA was dissolved in sterile $H_2O$ at a concentration of 0.5 mg/ml.

Electrophoresis

Genomic DNA was electrophoresed in agarose gels (0.8–1.2% agarose, Bio Rad Molecular biology-grade) using the Bio Rad Horizontal DNA Sub Cell. Tank buffers were 40 mM Tris acetate pH 8.0, 2 mM EDTA and 0.5 ug/ml ethidium bromide. DNA was visualized by UV transillumination. Size-cuts of digested genomic DNA were isolated using commercially available molecular weight markers as a guide. Slits across the gel lane were introduced, into which DEAE cellulose paper (NA45, Schleicher and Schuell) was placed. Electrophoresis was continued until all the fluorescence had absorbed to the paper. By sticking paper strips at intervals up the gel lane, discreet size fractions were isolated. A similar method was used to isolate DNA fragments from digested clones. The paper strips were washed 2× by vortexing in T.E. DNA was eluted by heating strips in TE supplemented to 1M with respect to NaCl and heating for 20 minutes at 65 deg. C. The buffer, containing the DNA of interest, was PCI extracted by standard procedures and ethanol precipitated. DNA was redissolved in sterile $H_2O$ and stored at −20 deg. C. until use.

Preparation of Vector DNA

Plasmid DNA's were prepared by standard procedures using alkaline lysis and cesium chloride gradient centrifugation (see Maniatis). All fragments were subcloned into either Bluescript+KS or BLUESCRIPT+SK vectors (Stratagene). Vector DNA (5 ug) was digested with a fourfold excess (20 units) of appropriate restriction endonuclease. DNA was PCI extracted by standard procedures and precipitated with ethanol. DNA was resuspended in 200 ul 10 mM Tris, pH 8.3, 5 mM MgCl and 0.1 mM $ZnCl_2$ heated to 75 deg. C. and quick cooled on ice. Calf intestinal alkaline phophatase (CIAP-Boehringer Mannheim-molecular biology grade) was added at 0.5 U/ug of DNA and incubated at 42 deg. C. for 30 minutes, 55 deg. C. for 30 minutes and heated to 75 deg. C. for 10 minutes before cooling on ice. An additional 2U of phosphatase was added and incubated as above. SDS was added to 0.1% and the mixture was extracted repeatedly with PCI, by standard procedures, and ethanol precipitated. DNA was dissolved at a concentration of 0.5 ug/ul in sterile $H_2O$, heated to 75 deg. C. for 15 minutes and allowed to cool to room temperature before storage at −20 deg. C. prior to use.

Ligation of Inserts to Vector DNA

Recombinant DNA molecules were prepared as follows. Vector and insert DNA were mixed at a 3:1 molar ratio. For a 10 ul ligation reaction, 2 ul of a solution containing 25 mM Tris HCl (pH 7.6), 50 mM $MgCl_2$, 5 mM DTT and 25% polyethylene glycol 8000 was added. One microliter each of 10 mM ATP and T4 DNA ligase (6–10 units) were added, the total volume was adjusted to 10 ul with sterile $H_2O$ and the mixture was incubated at 12 deg. C. for a minimum of 8 hours. Ligation of blunt ended molecules (typically for subcloning fragments) was performed using 1/10th the above concentration of ATP, double the amount of T4 DNA ligase and incubation at room temperature overnight. TE (90 ul) was added to ligation reactions, which were then purified by standard PCI extraction and ethanol precipitation. DNA was dissolved in 10–20 ul sterile $H_2O$ and stored at 4 deg. C. until its use for transformation of competent cells.

Preparation of Competent Bacterial Cells and DNA Transformation

Single colonies of *Escherichia coli* (strain JM 109) grown on M9 plates were inoculated into LB broth and grown overnight with shaking at 37 deg. C. Overnight cultures were diluted 1:100 with fresh LB broth. Cells were grown at 37 deg. C. with vigorous agitation to an O.D. 600 of 0.5. Cells were chilled on ice 10 minutes and centrifuged at 4,000× g for 10 minutes at 4 deg. C. The supernatant was aspirated off and cells were resuspended in the original volume with water followed by centrifugation as above. The process was again repeated with one half the original volume of $H_2O$. Cells were then resuspended in 1/50th the original volume of 10% glycerol and spun, as described above. Cells were resuspended in 1/500th the original volume of 10% glycerol (greater than $5 \times 10^{10}$ cells/ml) and either used directly for transformation with cloned genomic DNA or frozen for further subcloning of cloned DNA fragments. Transformation of bacterial cells with bovine genomic DNA/vector constructs was performed by high voltage electroporation using a GENE PULSER apparatus (Bio Rad). DNA (up to 500 ng in a volume of 2 ul or less was mixed with 40 ul competent cells on ice for 1 minute, added to a pre-chilled (4 deg. C.) electroporation cuvette and pulsed according to manufacturers settings. Immediately after pulsing, 1 ml SOC medium, pre-warmed to 37 deg. C., was added to cells which were transferred to 15 ml polypropylene culture tubes and shaken at 37 deg. C. for 1 hour. Cells were pelleted at 4,000× g for 10 minutes at room temperature, resuspended in 1 ml of LB amp and grown for 1 hour (approximately 3 cell doubling times), mixed with 0.4 ml of 100% glycerol, frozen in a dry ice ethanol bath and stored at −70 deg. C. Aliquots were then filtered for accurate CFU determination before plating for colonly hybridization.

Colony Hybridization

Transformed bacteria (3,000–5,000 cfu) were suspended in 2 ml of LB amp which was plated on LB amp plates (185 mm) and incubated at 37 deg. C. until colonies were 0.5–1.5 mm in diameter. Plates were chilled at 4 deg. C. for one hour prior to being overlain with 182 mM Nylon Filters (HYBOND N+ Amersham). Needle pricks were used to mark alignment of plates and filters. Filters were placed of 1.5M NaCl and 0.5M NaOH soaked filter paper for 7 minutes to denature bacterial DNA and transferred to filter paper soaked in 1.5M NaCl, 0.5M Tris HCl (pH 7.2) and 1 mM EDTA for 3 minutes. The final step was repeated one time, after which filters were rinsed briefly in 2× SSPE and dried at 80 deg. C. for 1 hour in an oven.

Southern Blotting of DNA and Filter Hybridization

Southern blots of agarose gels were prepared by the capillary method (see Maniatis et.al. 1982) to nylon membranes (HYBOND, N+ Amerham) using NaOH (0.4M) as the transfer buffer by the procedure recommended by the manufacturer. Filters (either blotted DNA or circles containing colony lifts) were pre-incubated in a solution containing 50% deionized formamide, 4× SSPE, 5× Denhards solution, 0.5% SDS and 500 ug/ml yeast RNA for 1–4 hours at 42 deg. C. Probe was added at a concentration not exceeding 10 ng/ml of prehybrid solution. Filters were incubated for 12–18 hours at 42 deg. C. Filters were washed once with 2× SSPE, 0.1% at room temperature for 30 minutes, twice for 15 minutes each with 1× SSPE, 0.1% SDS at 65 deg. C. and finally once for 10 minutes with 0.1× SSPE, 0.1% SDS at 65 deg. C. This latter step is a high stringency wash and was not always performed. Filters were dried and exposed to Kodak XAR X-ray film with a "LIGHTENING PLUS" intensifying screen (Kodak) at −70 deg. C. for varying amount of time.

Preparation of Radiolabeled Probes

Radiolabeled probes were prepared as originally described by Hodgson and Fisk (1987, NAR pg. 6295) without modification. Probes were purified by Sephadex G-75 chromotography (Pharmacia) and denatured at 100 deg. C. for 10 minutes prior to use in hybridizations.

Subcloning of Recombinant DNA's

To facilitate DNA sequence analysis, recombinant clones were thoroughly mapped with a number of restriction endonucleases. Fragments to be subcloned were isolated on DEAE cellulose paper as described above. Vector DNA was prepared with the appropriate restriction endonucleases and treated with CIAP as described above. Fragments were inserted into both BLUESCRIPT+SK and KS to facilitate sequencing from either end. Fragments whose ends were not compatible with restriction sites in the vector polylinker region were converted to blunt ended fragments by treatment with the Klenow fragment of *E coli* DNA polymerase I (see Maniatis for method). These fragments were then cloned into BLUESCRIPT KS digested with either Sma I or Eco RV whose restriction sites were also inside in the polylinker.

DNA Sequence Determination

Single colonies picked from M9 ampicillin plates (150 ug/ml) were used to inoculate 2 ml of LB/ampicillin media and grown overnight at 37 deg. C. Ten ul was then inoculated into 1 ml LB amp, shaken for 4 hours at 37 deg. C. before addition of 2 ul of helper-phage strain M13K07 and continued shaking for one hour. The culture was transferred to a disposable 50 ml culture tube containing 10 ml LB amp/Kanamycin (70 ug/ml) and shaken vigorously at 37 deg. C. for 12–18 hours. Following centrifugation at 10,000 rpm for 15 minutes, 8 ml of supernatant were added to 1.4 ml PEG/NaCl and incubated for a minimum of one hour on ice. Phage were pelleted for 20 minutes at 10,000× g and resuspended in 400 ul TE. DNA was isolated by standard PCI extraction and ethanol precipitation (procedure described above). DNA was dissolved in 50 ul sterile $H_2O$. Nucleotide sequence determination was performed using a commercially available T7 DNA polymerase based dideoxynucleotide system (SEQUENASE 2.0, United States Biochemicals) according to manufacturer's instructions. Nucleotide sequence ladders were resolved by polyacrylamide gel electrophoresis (see Maniatis). DNA sequences were assembled using the Microgenie sequence analysis package (Beckman). Data base searches were performed with the Genbank on line service (Intelligenetics Inc., Stanford) using the 'Fasta' sequence analysis program.

Although the foregoing invention has been described in some detail by way of illustration and example for purposes of clarity and understanding, it will be obvious that many changes and modifications may be practiced within the scope of the appended claims.

We claim:

1. A labeled or unlabeled Y-chromosome specific nucleic acid isolate which comprises the same sequence as that of either strand of an isolate selected from the group consisting of:
   (1) one or both strands of the PstI fragment SEQ ID NO:1; BtY1, and
   (2) one of both strands of the SacI fragment SEQ ID NO:3; BtY2.

2. The nucleic acid according to claim 1 which is radioactively labeled with $^3H$, $^{35}S$, $^{32}P$, or $^{125}I$.

3. The nucleic acid according to claim 1 which is non-radioactively labeled with biotin or bromodeoxyuridine.

4. The nucleic acid according to claim 1 wherein said nucleic acid is DNA.

5. The nucleic acid according to claim 1 wherein the nucleic acid is RNA.

6. The nucleic acid according to claim 4 which is radioactively labeled with $^3H$, $^{35}S$, $^{32}P$, or $^{125}I$.

7. The nucleic acid according to claim 4 which is non-radioactively labeled with biotin or bromodeoxyuridine.

8. The nucleic acid according to claim 5 which is radioactively labeled with $^3H$, $^{35}S$, $^{32}P$, or $^{125}I$.

9. The nucleic acid according to claim 5 which is non-radioactively labeled with biotin or bromodeoxyuridine.

10. The nucleic acid according to claim 4 wherein said DNA comprises the same sequence as that of either strand of a DNA selected from the group consisting of closed circular SEQ ID NO:1, BtY1 and linearized SEQ ID NO:1, BtY1.

11. The nucleic acid according to claim 10 which is radioactively labeled with $^3H$, $^{35}S$, $^{32}P$, or $^{125}I$.

12. The nucleic acid according to claim 10 which is non-radioactively labeled with biotin or bromodeoxyuridine.

13. The nucleic acid according to claim 4 wherein said DNA comprises the same sequence as that of either strand of a DNA selected from the group consisting of closed circular SEQ ID NO:3, BtY2 and linearized SEQ ID NO:3, BtY2.

14. The nucleic acid according to claim 13 which is radioactively labeled with $^3H$, $^{35}S$, $^{32}P$, or $^{125}I$.

15. The nucleic acid according to claim 13 which is non-radioactively labeled with biotin or bromodeoxyuridine.

16. A replicable vector comprising the nucleic acid isolate according to claim 1.

17. A replicable vector comprising a nucleic acid isolate encoding SEQ ID NO:3, BtY2.

18. A method for the determination of the presence or absence of a Y-chromosome in a ruminant, said method comprising:
   isolating DNA from a tissue or cell sample of a ruminant,
   immobilizing said DNA onto a support matrix,
   hybridizing the immobilized DNA with a nucleic acid isolate of claim 1 under conditions allowing the nucleic acid isolate to bind to complementary sequences,
   washing unbound nucleic acid isolate from the support matrix, and
   detecting nucleic acid isolate binding to DNA immobilized on the support matrix.

19. A method for determining the presence or absence of a Y-chromosome in fixed cells or chromosomes in the interphase or metaphase stages of nuclear division of a ruminant said method comprising:
   hybridizing said fixed cells or interphase or metaphase chromosomes of a ruminant with the nucleic acid isolate of claim 1 under conditions allowing the nucleic acid isolate to bind to complementary sequences,
   washing away unbound nucleic acid isolates, and
   detecting binding of the nucleic acid isolate to the complementary sequences in the fixed cells or interphase or
   detecting binding of the nucleic acid isolate to the complementary sequences in the fixed cells or interphase or metaphase chromosomes.

20. The method for determining the presence or absence of a Y-chromosome in a tissue or cell sample of a ruminant comprising:
   isolating DNA from a tissue or cell sample or a ruminant and denaturing the isolated DNA,
   annealing the denatured DNA with a synthetic polynucleotide comprising 12 or more nucleotides from the nucleic acid isolate of claim 1 under conditions allowing the synthetic polynucleotide to bind to a target DNA,
   amplifying the target DNA,
   immobilizing the amplified target DNA onto a support matrix,
   hybridizing the immobilized amplified target DNA with the nucleic acid isolate of claim 1 under conditions allowing the nucleic acid isolate to bind to complementary sequences,
   washing unbound nucleic acid isolate from the support matrix, and
   detecting binding of the nucleic acid isolate.

21. A method for determining the presence or absence of Y-chromosomes in a tissue or cell sample of a ruminant comprising:
   isolating DNA from a tissue or cell sample of a ruminant and denaturing the isolated DNA,
   annealing the denatured DNA with a synthetic polynucleotide comprising 12 or more nucleotides from the nucleic acid isolate of claim 1 under conditions allowing the synthetic polynucleotide to bind to a target DNA,
   incubating labeled nucleotide precursors with a DNA polymerase, amplifying the target DNA, hybridizing an amplified target DNA with a nucleic acid isolate of claim 1 under conditions allowing binding to complementary sequences, fractionating the sample by electrophoresis in a gel matrix, and detecting labeled nucleic acid isolates.

22. A method according to claim 18 wherein the nucleic acid isolate is labeled with a detectable marker selected from $^3H$, $^{35}S$, $^{32}P$, $^{125}I$, biotin or bromodeoxyuridine.

23. A method according to claim 19 wherein the nucleic acid isolate is labeled with a detectable marker selected from $^3H$, $^{35}S$, $^{32}P$, $^{125}I$, biotin or bromodeoxyuridine.

24. A method according to claim 20 wherein the nucleic acid isolate is labeled with a detectable marker selected from $^3H$, $^{35}S$, $^{32}P$, $^{125}I$, biotin or bromodeoxyuridine.

25. A method according to claim 21 wherein the nucleic acid isolate is labeled with a detectable marker selected from $^3H$, $^{35}S$, $^{32}P$, $^{125}I$, biotin or bromodeoxyuridine.

26. A kit for detecting the presence or absence of Y-chromosome specific sequences in a tissue or cell sample of a ruminant comprising the nucleic acid isolate according to claim 1 and a buffer.

27. The method of claim 18 wherein the ruminant is selected from the group consisting of bovine, ovine and caprine.

28. The method of claim 19 wherein the ruminant is selected from the group consisting of bovine, ovine and caprine.

29. The method of claim 20 wherein the ruminant is selected from the group consisting of bovine, ovine and caprine.

30. The method of claim 21 wherein the ruminant is selected from the group consisting of bovine, ovine and caprine.

* * * * *